US009579275B2

(12) United States Patent
Mu et al.

(10) Patent No.: US 9,579,275 B2
(45) Date of Patent: Feb. 28, 2017

(54) METHOD AND COMPOSITIONS FOR IMPROVING WEAR OF COLOR COSMETICS

(71) Applicant: ELC Management LLC, Melville, NY (US)

(72) Inventors: Weilin Mu, Albertson, NY (US); John R. Castro, Huntington Station, NY (US)

(73) Assignee: ELC Management, LLC, Melville, NY (US)

( * ) Notice: Subject to any disclaimer, the term of this patent is extended or adjusted under 35 U.S.C. 154(b) by 144 days.

(21) Appl. No.: 14/199,320

(22) Filed: Mar. 6, 2014

(65) Prior Publication Data

US 2014/0271511 A1    Sep. 18, 2014

Related U.S. Application Data

(60) Provisional application No. 61/792,159, filed on Mar. 15, 2013.

(51) Int. Cl.
| | | |
|---|---|---|
| *A61K 8/00* | (2006.01) | |
| *A61K 8/81* | (2006.01) | |
| *A61K 8/26* | (2006.01) | |
| *A61K 8/891* | (2006.01) | |
| *A61Q 1/10* | (2006.01) | |
| *A61Q 19/00* | (2006.01) | |

(52) U.S. Cl.
CPC .............. *A61K 8/8182* (2013.01); *A61K 8/26* (2013.01); *A61K 8/891* (2013.01); *A61Q 1/10* (2013.01); *A61Q 19/00* (2013.01); *A61K 2800/594* (2013.01); *A61K 2800/884* (2013.01)

(58) Field of Classification Search
CPC ...... A61K 8/25; A61K 8/8111; A61K 8/8123; A61K 8/87; A61K 8/88; A61K 8/893; A61K 8/894; A61Q 1/06
See application file for complete search history.

(56) References Cited

U.S. PATENT DOCUMENTS

| | | |
|---|---|---|
| 3,439,088 A | 4/1969 | Edman |
| 3,818,105 A | 6/1974 | Coopersmith et al. |
| 4,584,355 A | 4/1986 | Blizzard et al. |
| 5,330,747 A | 7/1994 | Krzysik |
| 6,060,072 A | 5/2000 | Konik et al. |
| 6,503,495 B1 | 1/2003 | Alwattari et al. |
| 6,964,773 B1 | 11/2005 | Morrison |
| 7,879,346 B2 | 2/2011 | Lee et al. |
| 2002/0085986 A1 | 7/2002 | De La Poterie et al. |
| 2004/0141933 A1 | 7/2004 | Luo et al. |
| 2004/0156804 A1 | 8/2004 | Poterie et al. |
| 2004/0161395 A1 | 8/2004 | Patil et al. |
| 2006/0110346 A1* | 5/2006 | Lu ........................ A61K 8/31 424/64 |

FOREIGN PATENT DOCUMENTS

JP        2006176453 A        7/2006

OTHER PUBLICATIONS

PCT International Search Report; International Application No. PCT/US2014/021273; Completion Date: Jun. 26, 2014; Mailing Date: Jun. 26, 2014.
PCT Written Opinion of the International Searching Authority; International Application No. PCT/US2014/021273; Completion Date: Jun. 26, 2014; Mailing Date: Jun. 26, 2014.
Mono Eyeshadow; Mintel GNPD; Record ID: 680429; Gemey Maybelline; Maybelline Expert Wear; Colour Cosmetics; Eye Colour Cosmetics—Eye Shadow; France; Mar. 2007.
Product Information; Healthcare; Dow Corning®BIO-PSA; Ref. No. 52-1052A-01; Standard Silicone Adhesives; 4 pages; Jul. 2008.
Sales Specification—International Specialty Products; www.ispcorp.com; Report ID: WH0294; Ganex V-220 Chemical Description: Alkylated Polyvinyl Pyrrolidone with Eicosene 30/70 ratio; 1 page; Feb. 2013.
Supplemental European Search Report; EP14768249; Completion Date: Jun. 21, 2016; Mailing Date: Jun. 29, 2016.

* cited by examiner

*Primary Examiner* — Nannette Holloman
(74) *Attorney, Agent, or Firm* — Julie Blackburn

(57) ABSTRACT

A composition comprising at least one non-sensitizing pressure sensitive adhesive that is the polycondensate of a silanol endblocked polydimethylsiloxane and a silicate resin; at least one copolymer of vinyl pyrrolidone and a long chain alpha olefin; at least one montmorillonite mineral; and at least one volatile solvent; and a related methods and kits.

20 Claims, No Drawings

METHOD AND COMPOSITIONS FOR IMPROVING WEAR OF COLOR COSMETICS

CROSS-REFERENCE TO RELATED APPLICATIONS

The present application claims priority from U.S. Provisional Application No. 61/792,159, filed Mar. 15, 2013.

TECHNICAL FIELD

The invention is in the field of compositions for improving wear of cosmetics, in particular color cosmetics, and related methods.

BACKGROUND OF THE INVENTION

Consumers who wear color cosmetics that are applied daily, at a minimum, want the cosmetic to remain on the surface to which it is applied for a reasonable period of time. For color cosmetics such as foundation, eye shadow, or blush, it is desirable that the color cosmetic remain on the skin for the entire day. Modern women are busy—either working in, or outside, the home. Most do not have the time or inclination to reapply cosmetics. Color cosmetics that are applied once-a-day and remain fresh and color true all day are the price of entry.

Primers are popular today and have the same principle as paint primers—to prepare the keratin surface so that the color cosmetic that is applied exhibits better adhesion and provides more even, homogenous color. Primers are particularly useful with color cosmetics that are applied in powder form. For example, eye shadow is very often in a powder form. Powder is easy to apply. It is also "forgiving", which means that if the consumer makes a mistake in applying the shadow to an area where it is not desired, it can easily be removed. However, one problem with powder eye shadow is that it may crease or wear off during the day. Shadows that have glittery effects are particularly prone to flaking off over time.

Accordingly there is a need for primer compositions that will be applied to a keratin surface prior to application of color cosmetic that will improve the wear and adhesion of the color cosmetic to the skin.

SUMMARY OF THE INVENTION

The invention is directed to a composition comprising, by weight of the total composition:
   at least one non-sensitizing pressure sensitive adhesive that is the polycondensate of a silanol endblocked polydimethylsiloxane and a silicate resin;
   at least one copolymer of vinyl pyrrolidone and a long chain alpha olefin;
   at least one montmorillonite mineral; and
   at least one volatile solvent;
wherein the ratio of the pressure sensitive adhesive to the copolymer in the final composition is at least 2 to 1 and the polycondensate, after formulation into the composition, is not reactive with the copolymer or the montmorillonite mineral.

The invention is also directed to a method for improving color retention of a color cosmetic composition applied to a keratinous surface, comprising the steps of:
   first applying to the surface a spreadable primer composition comprising:
      at least one non-sensitizing pressure sensitive adhesive that is the polycondensate of a silanol endblocked polydimethylsiloxane and a silicate resin;
      at least one copolymer of vinyl pyrrolidone and a long chain alpha olefin;
      at least one laminar montmorillonite mineral; and
      at least one volatile solvent;
   wherein the ratio of the pressure sensitive adhesive to the copolymer in the final composition is at least 2 to 1 and the polycondensate, after formulation into the composition, is not reactive with the copolymer or the montmorillonite mineral;
   allowing the primer composition to dry for at least 1 second;
   followed by application of the color cosmetic product directly over the primer composition.

The invention is further directed to a kit for storing and dispensing color cosmetics comprising:
   A first receptacle containing a primer composition comprising at least one non-sensitizing pressure sensitive adhesive that is the polycondensate of a silanol endblocked polydimethylsiloxane and a silicate resin; at least one copolymer of vinyl pyrrolidone and a long chain alpha olefin; at least one laminar montmorillonite mineral; and at least one volatile solvent; wherein the ratio of the pressure sensitive adhesive to the copolymer in the final composition is at least 2 to 1 and the polycondensate, after formulation into the composition, is not reactive with the copolymer or the montmorillonite mineral; and
   A second receptacle containing a color cosmetic composition.

DETAILED DESCRIPTION

All percentages mentioned herein are percentages by weight unless otherwise indicated. The composition of the invention comprises a number of essential ingredients. It is a preferably a spreadable composition, that may be in the form of a solid, semi-solid, or liquid. The composition may be anhydrous or in the form of an aqueous composition. If the latter, an emulsion or solution is preferred. The emulsion may be water in oil, or oil in water. The term "spreadable" means that the composition is of a consistency that it may be picked up and applied with the fingers or an applicator and will spread or blend into the skin or keratin surface to which it is applied.

The Polycondensate

The composition of the invention contains at least one non-sensitizing pressure sensitive adhesive that is the polycondensate of a silanol endblocked polydimethylsiloxane and a silicate resin. The polycondensate is present in an amount ranging from about 0.01 to 45%, preferably from about 0.05 to 40%, more preferably from about 0.1 to 25%.

The term "non-sensitizing" means that the pressure sensitive adhesive polycondensate is hypoallergenic. The silanol endblocked polydimethylsiloxane has terminal hydroxyl groups on one or both terminal ends. The polydimethylsiloxane is preferably linear, and may have from about 5 to 1 million —[Si—O]— repeat units. Most preferred is where the polydimethylsiloxane is linear, has hydroxyl groups on the alpha and omega terminus, and has from about 5 to 500,000 repeat units.

One example of a polycondensate suitable for use in the composition may be purchased from Dow Corning under the tradename 7-4405, having the CTFA name dimethicone silylate. In a most preferred embodiment the dimethicone silylate is in the form of a mixture of 40 parts dimethicone silylate and 60 parts isododecane.

The Copolymer of Vinyl Pyrrolidone and Long Chain Alpha Olefin

The composition also comprises at least one copolymer of vinyl pyrrolidone and a long chain alpha olefin. The copolymer may be present in amounts ranging from about 0.001 to 40%, preferably from about 0.01 to 35%, more preferably from about 0.05 to 30% by weight of the total composition.

Preferably the copolymer is a solid or semi-solid at room temperature. The copolymer of vinyl pyrrolidone contains repeat units of the following formula, where R is H or C1-10 straight or branched chain, saturated or unsaturated alkyl which may be substituted with hydrogen, halogens, etc.

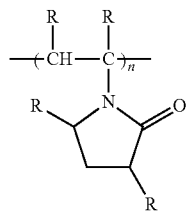

The long chain alpha olefin may contain from 14-40 carbon atoms, and may be in the linear or branched form. Examples of suitable alpha olefins include eicosene, isoeicosene, decene, octadecene, and the like.

Preferred is where the copolymer is PVP/eicosene copolymer sold by International Specialty Products under the trademark Ganex.

The Montmorillonite Mineral

The composition comprises at least one montmorillonite mineral in an amount ranging from about 0.01 to 80%, preferably from about 0.1 to 75%, more preferably from about 0.5 to 70% by weight of the total composition. The montmorillonite mineral may be substituted with quaternary ammonium compounds, such as Quaternium-18 or distearyl dimonium chloride and the like. The montmorillonite mineral is preferably in the form of platelets or sheets that may or may not be interconnected.

Suitable montmorillonite minerals include synthetic or natural metal silicates such sodium, potassium, magnesium, aluminum, lithium, zinc, iron, calcium, or beryllium silicates or mixtures thereof. Natural metal silicates are also known as "hectorites" or "bentonites". In general, a formula for some types of clays in the montmorillonite group is as follows:

$(Na,Ca)(Al,Mg)_6(Si_4O_{10})_3(OH)_{6-x}H_2O$ where x is the variable amount of water that may be present.

Particularly preferred is where the montmorillonite mineral is Quaternium-18 hectorite or Disteardimonium hectorite.

The Volatile Solvent

The composition of the invention comprises at least one volatile solvent in amounts ranging from about 0.1 to 85%, preferably from about 0.5 to 75%, more preferably from about 0.5 to 60% by weight of the total composition. Suitable volatile solvents generally have a viscosity ranging from about 0.5 to 5 centistokes 25° C. and include linear silicones, cyclic silicones, paraffinic hydrocarbons, or mixtures thereof.

Linear or cyclic volatile silicones include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst), methyl trimethicone (1.5 cst) and mixtures thereof are suitable.

Cyclic, linear or branched volatile silicones are available from various commercial sources including Dow Corning Corporation and General Electric. The Dow Corning linear volatile silicones are sold under the tradenames Dow Corning 244, 245, 344, and 200 fluids. Suitable branched volatile silicones include alkyl trimethicones such as methyl trimethicone, a branched volatile silicone having the general formula:

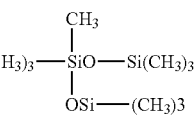

Also suitable as the volatile solvent are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

Coconut alkanes, sold under the trademark "Vegelight" are also suitable volatile solvents.

Other Ingredients

The composition of the invention may also comprise a variety of other ingredients including those further set forth herein.

1. Non-Volatile Oil

The composition may additionally comprise one or more non-volatile oils. If present suggested ranges are from about 0.1 to 85%, preferably from about 0.5 to 75%, more preferably from about 1 to 60%. The nonvolatile oils generally have a viscosity of greater than about 5 to 10 centistokes at 25° C., and may range in viscosity up to about 1,000,000 centipoise at 25° C. Examples of nonvolatile oils include, but are not limited to mono-, di-, and triesters formed by the reaction of mono-, di-, or tricarboxylic acids with aliphatic or aromatic alcohols. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of such oils include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Also suitable are various types of nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Naturally occurring oils from animal and vegetable sources are also suitable, including but not limited to Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable are nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Examples include dimethicone, phenyl dimethicone, diphenyl dimethicone, phenyl trimethicone, or trimethylsiloxyphenyl dimethicone, or alkyl dimethicones such as cetyl dimethicone, and the like.

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored (for example white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, calcium silicate, cellulose, chalk, corn starch, diatomaceous earth, fuller's earth, glyceryl starch, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

The composition may contain one or more structuring agents in the form of waxes, polymers, and the like. Suggested ranges are from about 0.1 to 45%, preferably from about 0.5 to 40%, more preferably from about 1 to 35% by weight of the total composition. Suitable structuring agents are synthetic or natural waxes having a melting point ranging from 30 to 100° C. and include polyethylene, trihydroxystearin, vegetable waxes such as bayberry, candelilla, ozokerite, and the like.

The composition may include other ingredients such as preservatives, antioxidants, structuring agents, and the like.

The invention will be further described in connection with the following examples which are set forth for the purposes of illustration only.

Example 1

An eye shadow primer composition was made as follows:

| Ingredient | % by wt |
|---|---|
| Dimethicone | QS |
| Isododecane | 25.00 |
| Talc | 8.00 |
| Dimethicone silylate | 6.40 |
| Trihydroxystearin | 5.00 |
| Disteardimonium hectorite | 4.00 |
| Kaolin | 3.00 |
| Hydrogenated polyisobutene | 2.50 |
| Polyethylene | 2.00 |
| VP/Eicosene copolymer | 2.00 |
| Trioctyl dodecyl citrate | 1.65 |
| Titanium dioxide | 1.10 |
| Triethylhexanoin | 1.00 |
| Tocopherol acetate | 0.50 |
| Silica | 0.34 |
| Propylene carbonate | 0.32 |
| Aluminum hydroxide | 0.15 |
| Caprylyl glycol | 0.15 |
| Ethylene/methacrylate copolymer | 0.15 |
| Bisabolol | 0.10 |
| Lecithin | 0.10 |
| PEG-40 stearate | 0.10 |
| Sorbitan sesquioleate | 0.10 |
| Stearic acid | 0.10 |
| Glycyrrhetinic acid | 0.05 |
| Antioxidant | 0.05 |
| Bismuth oxychloride | 0.03 |
| Iron oxides | 0.02 |
| Isopropyl titanium triisostearate | 0.01 |

Example 2

The composition of Example 1 was tested to determine effect on extending the wear of eye shadow. Twelve adult women were recruited from a local population. Excluded were women that were pregnant or lactating, had any dermatological conditions, systemic illness, or were using retinoids, anti-histamines, or similar agents.

Test subjects were instructed to wear no moisturizer or makeup the days of testing. Subjects applied Maybelline Mono Eye Shadow alone to the right eye. The ingredients in the formula, as set forth on the package label are:

Talc, nylon-12, synthetic fluorphlogopite, triisostearin, phenyl trimethicone, magnesium stearate, dimethicone, calcium sodium borosilicate, phenoxyethanol, cetyl dimethicone, synthetic wax, methylparaben, trimethylsiloxysilicate, ethylparaben, propylparaben, isobutylparaben, butyl paraben, polyethylene terephthalate, polymethymethacrylate, +/− may contain (mica, CI77891/titanium dioxide, iron oxides (CI77492, CI77499, CI77491), CI 77007/ultramarines, CI 77000/aluminum powder, CI77288/chromium oxide greens, CI77289/chromium hydroxide green, CI77510/ferric ferrocyanide, CI77163/bismuth oxychloride, CI19140/yellow 5 lake, CI 16035/red 40 lake, CI 42090/blue 1 lake.

On the left eye, the primer composition of Example 1 was applied, allowed to dry, then the eye shadow was applied by the investigator using the applicators provided.

The results are set forth in the table below, and show that the primer of the invention provided a significant improvement in color retention and reduction increasing when compared to the eye shadow alone.

|  | Eye shadow alone | | Primer + Eye shadow | |
| --- | --- | --- | --- | --- |
|  | Color Retention | Creasing | Color Retention | Creasing |
| Immediate | 100% | None | 100% | None |
| 2 hours | 93% | None | 97% | None |
| 4 hours | 82% | Mild | 92% | None |
| 6 hours | 74% | Mild | 89% | Minimal |
| 8 hours | 71% | Moderate | 86% | Minimal |
| 10 hours | 68% | Moderate | 84% | Mild |
| 12 hours | 65% | Moderate | 80% | Mild |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A two layer composition for application to a keratin surface comprising a first applied primer composition comprising, by weight of the total composition:
   0.1-25% of at least one non-sensitizing pressure sensitive adhesive that is the polycondensate of a silanol endblocked polydimethylsiloxane and a silicate resin;
   0.01-30% of at least one copolymer of vinyl pyrrolidone and a long chain alpha olefin;
   0.01-70% of at least one montmorillonite mineral; and
   0.1-60% of at least one volatile solvent;
wherein the ratio of the pressure sensitive adhesive to the vinyl pyrrolidone copolymer in the final composition is at least 2 to 1; and a second applied color cosmetic composition wherein the first applied primer composition causes from 80 to 100% of the second applied color cosmetic composition to remain on the keratin surface for at least 12 hours after application.

2. The composition of claim 1 wherein the silanol endblocked polydimethylsiloxane is a linear non-volatile polydimethylsiloxane having from 5 to 1 million Si—O repeat units and terminal hydroxyl groups.

3. The composition of claim 1 wherein the silanol endblocked polydimethylsiloxane has a viscosity ranging from 10 to 1 million centistokes at 20° C.

4. The composition of claim 1 wherein the silicate resin is an MQ resin with optional D or T functional units.

5. The composition of claim 1 wherein the polycondensate is dimethicone silylate.

6. The composition of claim 5 wherein the copolymer is a copolymer of vinyl pyrrolidone and a long chain alpha olefin having from 5 to 40 carbon atoms.

7. The composition of claim 5 wherein the copolymer is a copolymer of vinyl pyrrolidone and eicosene.

8. The composition of claim 7 wherein the volatile solvent is isododecane, isohexadecane, or mixtures thereof.

9. The composition of claim 7 wherein the volatile solvent comprises a mixture of a linear or cyclic silicone and a hydrocarbon or coconut based alkane.

10. The composition of claim 8 wherein the montmorillonite mineral is reacted with a quaternary ammonium compound that is optionally substituted with a fatty alkyl group.

11. The composition of claim 10 wherein the montmorillonite mineral is disteardimonium hectorite.

12. A method for improving color retention of a color cosmetic composition applied to a keratinous surface, comprising the steps of:
   first applying to the surface a spreadable primer composition comprising:
      at least one non-sensitizing pressure sensitive adhesive that is the polycondensate of a silanol endblocked polydimethylsiloxane and a silicate resin;
      at least one copolymer of vinyl pyrrolidone and a long chain alpha olefin;
      at least one laminar montmorillonite mineral; and
      at least one volatile solvent;
   wherein the ratio of the pressure sensitive adhesive to the copolymer in the final composition is at least 2 to 1 and the polycondensate, after formulation into the composition, is not reactive with the copolymer or the montmorillonite mineral;
   allowing the primer composition to dry for at least 1 second;
   followed by application of the color cosmetic product directly over the primer composition.

13. The method of claim 12 wherein the color cosmetic is an eye shadow.

14. The method of claim 12 wherein the polycondensate comprises dimethicone silylate.

15. The method of claim 12 wherein the volatile solvent comprises isododecane.

16. A kit for color cosmetics comprising:
   A first receptacle containing a spreadable primer comprising at least one non-sensitizing pressure sensitive adhesive that is the polycondensate of a silanol endblocked polydimethylsiloxane and a silicate resin; at least one copolymer of vinyl pyrrolidone and a long chain alpha olefin; at least one laminar montmorillonite mineral; and at least one volatile solvent; wherein the ratio of the pressure sensitive adhesive to the copolymer in the final composition is at least 2 to; and A second receptacle containing a color cosmetic composition; wherein when the compositions in the first and second receptacles are applied to a keratin surface in order, the first composition causes from 80 to 100% of the second composition to remain adherent to the keratin surface for at least 12 hours after application.

17. The kit of claim 16 wherein the second receptacle is an eye shadow.

18. The kit of claim 17 wherein the second receptacle is a foundation makeup.

19. The kit of claim 17 wherein the polycondensate is dimethicone silylate.

20. The kit of claim 17 wherein the polycondensate is dimethicone silylate, the copolymer of vinyl pyrrolidone and the long chain alpha olefin is VP/eicosene copolymer, the volatile solvent comprises isododecane.

* * * * *